United States Patent [19]

Novinkov

[11] Patent Number: 5,931,816
[45] Date of Patent: Aug. 3, 1999

[54] SYRINGE AND METHOD OF USING SAME

[76] Inventor: Oleg L. Novinkov, 8950 Chimney Rock, #130, Houston, Tex. 77096

[21] Appl. No.: 09/047,020

[22] Filed: Mar. 24, 1998

[51] Int. Cl.$^6$ ..................................................... A61M 5/00
[52] U.S. Cl. ........................... 604/187; 604/181; 604/506
[58] Field of Search ...................................... 604/208, 181, 604/182, 191, 187, 218, 228, 232, 234, 506

[56] References Cited

U.S. PATENT DOCUMENTS

| | | | |
|---|---|---|---|
| 1,105,275 | 7/1914 | Ingalls | 604/143 |
| 1,267,616 | 5/1918 | Abramovitz | 604/217 |
| 4,232,670 | 11/1980 | Richter et al. | 128/224 |
| 4,505,701 | 3/1985 | Navato | 604/143 |
| 4,693,709 | 9/1987 | George et al. | 604/212 |
| 4,795,444 | 1/1989 | Hasegawa et al. | 604/218 |
| 4,798,596 | 1/1989 | Muhlbuer | 604/218 |
| 4,979,943 | 12/1990 | Trenner | 604/110 |
| 5,062,834 | 11/1991 | Gross et al. | 604/143 |
| 5,085,638 | 2/1992 | Farbstein et al. | 604/110 |
| 5,236,355 | 8/1993 | Brizzolara et al. | 433/80 |
| 5,250,030 | 10/1993 | Corsich | 604/110 |
| 5,370,626 | 12/1994 | Farris | 604/187 |
| 5,538,506 | 7/1996 | Farris et al. | 604/187 |
| 5,674,205 | 10/1997 | Pasricha et al. | 604/232 |
| 5,779,668 | 7/1998 | Grabenkort | 604/89 |

*Primary Examiner*—Wynn Wood Coggins
*Assistant Examiner*—LoAn H. Thanh
*Attorney, Agent, or Firm*—Keeling Law Firm

[57] ABSTRACT

My invention is a syringe which does not require the use of prior art plunger mechanisms to function (and its method of use). My syringe generally comprises the main body section and fluid transmission means, usually a needle, of prior art syringes. A seal slidingly disposed within the main body section prohibits fluid flow through the main body section. Although this seal corresponds to the plunger seal used in prior art syringes, my syringe does not include a plunger rod which is an essential part of prior art syringes. In the preferred embodiment, a second body section is attached to the main body section at the main body section end opposite the fluid transmission means. Fluid communication is provided between main body section and second body section. The end of second body section opposite the attachment to main body section must be open and must be sized to allow the insertion of a person's finger therein so that the finger may substantially cover the opening. With this syringe, a medical provider may insert his finger into second body section through the opening so that his finger substantially covers the opening. By rubbing the inner surface of second body section, the medical provider can cause the seal to slide within the main body section and the syringe to inject or suction fluid, depending on the direction of the rubbing motion. In the preferred embodiment, second body section is selectively removably attached to main body section so that second body section may be re-used multiple times with different main body sections.

7 Claims, 2 Drawing Sheets

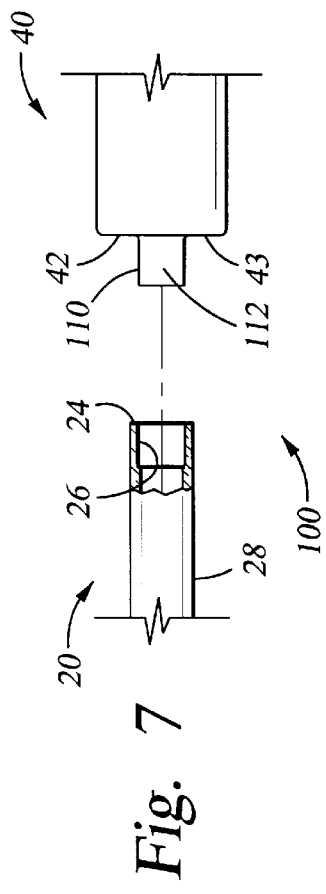
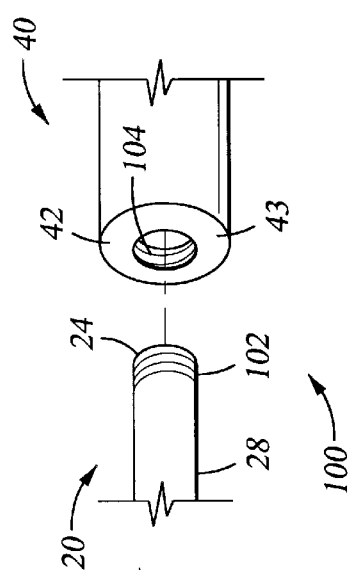
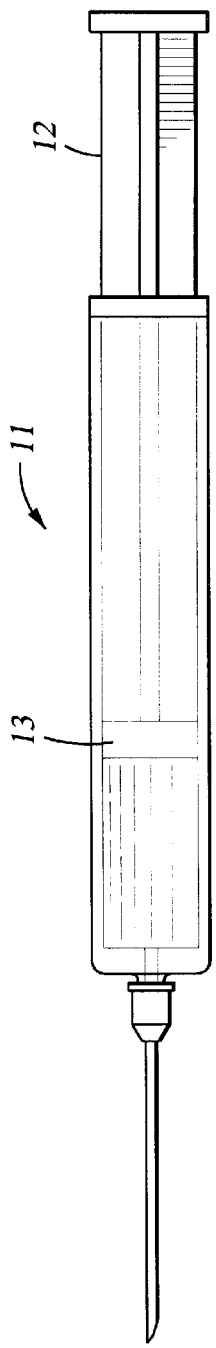
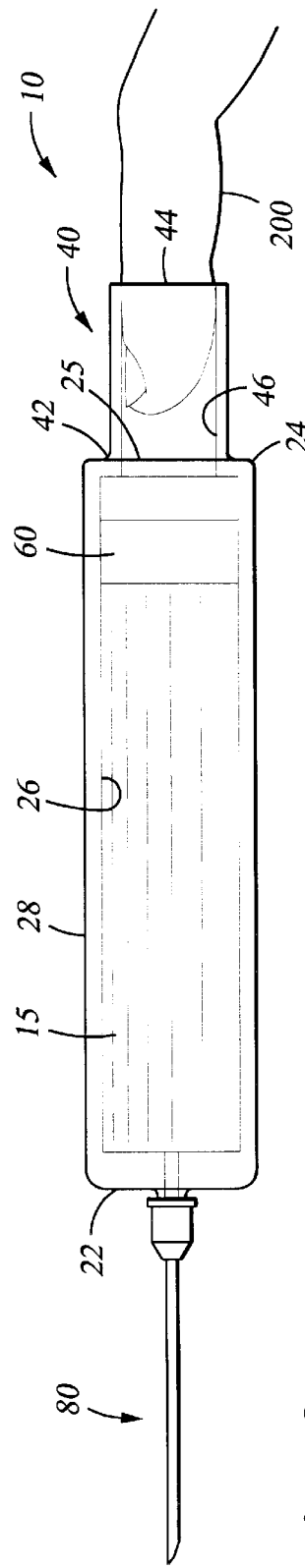

SYRINGE AND METHOD OF USING SAME

BACKGROUND OF THE INVENTION

1. Field of Invention

In general, this invention relates to syringes. More specifically, this invention relates to syringes which can be used without a plunger mechanism. This invention also specifically relates to a method of use for such syringes.

Typical syringes include a plunger mechanism which is slidingly disposed within the tubular body of the syringe. The plunger mechanism is then pushed or pulled by a user in order to inject medical solution from the syringe or in order to suction fluids into the syringe.

Plunger mechanisms normally consist of a sliding seal and an attached rod. Because the rod is accessible to a user from outside of the body of the syringe, a user may easily push or pull on the rod thereby causing the seal to slide within the syringe's body. In its completely retracted state, the rod typically nearly doubles the overall size of the syringe.

Some syringes are sold pre-filled with a specific amount of medical solution and with the plunger mechanism already disposed within the body of the syringe. These syringes are usually enclosed in a package. Because the plunger mechanism is already disposed within the syringe body and the rod is at least partially, if not fully, retracted in order to provide space for the solution within the syringe body, the syringe takes up a large amount of space all of which the package must enclose. The conservation of space is important to medical providers. And, in specific instances such as battlefield applications and space flight, the conservation of space is vital.

Thus, it would be beneficial to the prior art to provide a pre-filled syringe which takes up less space than comparable prior art syringes. Specifically, it would be beneficial to the prior art to provide a pre-filled syringe that neither includes nor requires the prior art plunger mechanism to function thereby decreasing the overall size of the syringe and of the packaging for the syringe.

Since the omission of a part would decrease the price and cost of a syringe, it would also be beneficial to the prior art to provide a syringe (pre-filled or not) that does not require the prior art plunger mechanisms to function.

Furthermore, in instances such as battlefield or emergency personnel applications, time is normally critical. The amount of time a medical provider spends in preparing a syringe for injection could determine the life or death of a patient. For unassembled prior art syringes, a medical provider must first insert the plunger mechanism within the body of the syringe and then fill the syringe with the correct amount of medical solution. These steps are usually cumbersome and may take a substantial amount of time, specially in stressful life or death situations. It would thus be beneficial to the prior art to provide a syringe which does not require a prior art plunger mechanism or its insertion into the syringe body and which is pre-filled with medical solution. Such a syringe would also simplify the injection or suction procedures.

2. Related Art

There are a variety of syringe structures known to the prior art. Illustrative of such prior art syringes which do not utilize a common prior art plunger mechanism are U.S. Pat. No. 519,014 issued to Beck on May 1, 1894; U.S. Pat. No. 1,105,275 issued to Ingalls on Jul. 28, 1914; U.S. Pat. No. 1,267,616 issued to Abramovitz on May 28, 1918; U.S. Pat. No. 4,505,701 issued to Navato on Mar. 19, 1985; U.S. Pat. No. 5,062,834 issued to Gross et al. on Nov. 5, 1991; U.S. Pat. No. 5,370,626 issued to Farris on Dec. 6, 1994; and U.S. Pat. No. 5,538,506 issued to Farris et al. on Jul. 23, 1996. None of these syringes, however, discloses the structure of or the method utilized with the Applicant's syringe.

SUMMARY OF THE INVENTION

Accordingly, the objectives of this invention are to provide, inter alia a syringe that:

- is pre-filled and takes up less space than comparable prior art syringes;
- is pre-filled and neither includes nor requires the plunger mechanism of prior art syringes thereby decreasing the overall size of the syringe and of the packaging for the syringe;
- is less costly because it does not require or include the plunger mechanism of prior art syringes to function; and
- is pre-filled and does not require a prior art plunger mechanism and its insertion into the syringe body for operation thereby decreasing the preparation time for use and simplifying the injection and suction procedures.

Other objects of the invention will become apparent from time to time throughout the specification hereinafter disclosed.

To achieve such improvements, my invention is a syringe which does not require the use of prior art plunger mechanisms to function (and its method of use). My syringe generally comprises the main body section and fluid transmission means, usually a needle, of prior art syringes. A seal slidingly disposed within the main body section prohibits fluid flow through the main body section. Although this seal corresponds to the plunger seal used in prior art syringes, my syringe does not include a plunger rod which is an essential part of prior art syringes. In the preferred embodiment, a second body section is attached to the main body section at the main body section end opposite the fluid transmission means. Fluid communication is provided between main body section and second body section. The end of second body section opposite the attachment to main body section must be open and must be sized to allow the insertion of a person's finger therein so that the finger may substantially cover the opening. With this syringe, a medical provider may insert his finger into second body section through the opening so that his finger substantially covers the opening. By rubbing the inner surface of second body section, the medical provider can cause the seal to slide within the main body section and the syringe to inject or suction fluid, depending on the direction of the rubbing motion. In the preferred embodiment, second body section is selectively removably attached to main body section so that second body section may be re-used multiple times with different main body sections.

BRIEF DESCRIPTION OF THE DRAWINGS

FIG. 6 is an isometric view of one embodiment of body attachment means.

FIG. 7 is an isometric view of a second embodiment of body attachment means.

FIG. 8 is an elevational view of a prior art syringe.

FIG. 9 is an elevational view of a different embodiment of the syringe.

DETAILED DESCRIPTION OF THE INVENTION

Figure 1:
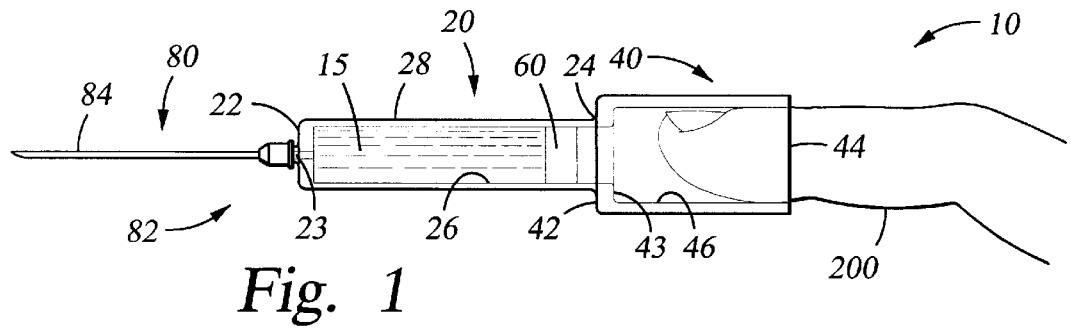
FIG. 1 is an elevational view of the syringe with one embodiment of second body section.

The syringe of my invention is generally shown in FIGS. 1–5 and 9 as reference numeral 10. In general, syringe 10 comprises a first body section 20, a second body section 40, a seal 60, and a fluid transmission means 80. For purposes of comparison, a prior art syringe 11 is shown in FIG. 8. It is of note that such prior art syringe 11 does not include a second body section 40 and includes a plunger rod 12, which is importantly not contained in syringe 10.

Turning to FIGS. 1–5 and 9, first body section 20 is tubular in shape and hollow. First body section 20 includes a first body section first end 22, a first body section second end 24, a first body section inner surface 26, and a first body section outer surface 28. Preferably, first body section 20 has a circular cross-sectional area. Also preferably, such circular cross-sectional area is uniform from first body section first end 22 to first body section second end 24.

Although first body section first end 22 is predominantly enclosed, first body section first end 22 includes a first end opening 23. First end opening 23 facilitates the attachment of fluid transmission means 80. Preferably, first end opening 23 is circular in shape and is co-axially aligned with the tubular shape of first body section 20. First body section second end 24 is open. In one preferred embodiment as shown in FIGS. 1–4, the cross-sectional area size of first body section 20 is such that a person could not insert a finger 200 into first body section 20 through first body section second end 24. In another preferred embodiment as shown in FIGS. 5 and 9, the cross-sectional area size of first body section 20 is such that a person could insert a finger 200 into first body section 20 through first body section second end 24.

Second body section 40 is hollow and includes a second body section first end 42, a second body section second end 44, and a second body section inner surface 46. Second body section second end 44 is open. Importantly, the length and cross-sectional area of second body section 40 must be sized and shaped to allow the insertion of a person's finger 200 through second body second end 44 and to allow the person's finger 200 to extend substantially within second body section 40 preferably substantially to second body section first end 42. In addition, the length and cross-sectional area of second body section 40 must be sized and shaped to allow a person's finger 200 to substantially cover the opening of second body section second end 44 when such person's finger 200 is inserted within second body section 40.

Thus, second body section 40 must be sized to have such dimensions. According to NASA Reference Publication 1024, *Anthropometric Source Book Volume II: A Handbook of Anthropometric Data*, published by NASA in 1978, the range of human middle finger diameter sizes at the middle finger's metacarpal III (or large joint) is from 1.8 cm. (1st percentile in two surveys) to 2.5 cm. (99th percentile in four surveys). Thus, for syringe 10 to be used by the majority, if not all, of the human population, second body section first and second ends, 42 and 44, may have a diameter of at least 2.5 cm. measured at second body section inner surface 46. However, noting that the diameter of a person's finger anywhere from the fingertip to the metacarpal bone is normally less than the diameter at the metacarpal bone of the same finger and noting that the majority of people have metacarpal III diameters within the range of 1.8 cm. to 2.5 cm., it is reasonable to construct second body section 40 so that second body section first and second ends, 42 and 44, have a diameter of at least 2.0 cm. ±0.2 cm. measured at second body section first end 46. Such a diameter size will ensure that syringe 10 may be useable by a great majority of the human population.

It is noted that a user may, and in most instances will, be wearing a medical glove, or a similar type of protection, on his/her hand while handling any syringe so that the relevant part of such glove will surround finger 200. Although, for purposes of clarity, such a glove is not shown in the Figures, it is understood that syringe 10 and its method of use described herein do function if such a glove surrounds finger 200.

First body section 20 is attached to and is in fluid communication with second body section 40. In the preferred embodiment, second body section first end 42 is attached to first body section second end 24.

In one preferred embodiment as shown in FIG. 1, second body section 40 is tubular in shape and has a circular cross-sectional area. In this embodiment, the circular cross-sectional area of second body section 40 is uniform from second body section first end 42 to second body section second end 44. Also in this embodiment, the diameter of second body section 40 is larger than the diameter of first body section 20. Second body section first end 42 thus defines a second body shoulder 43 which extends from and attaches second body section 40 to first body section 20 at first body section second end 24. In this embodiment, second body shoulder 43 is substantially perpendicular to both first body section outer surface 28 and second body section inner surface 46. Preferably, second body shoulder 43 is sized and constructed so that second body section 40 is co-axially aligned with first body section 20.

Figure 2:
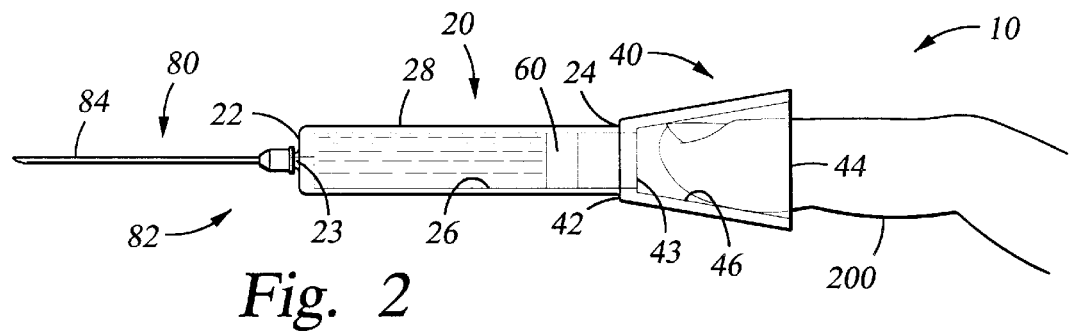
FIG. 2 is an elevational view of the syringe with a second embodiment of second body section.

In another preferred embodiment as shown in FIG. 2, second body section 40 is frustoconical in shape and has a circular cross-sectional area. In this embodiment, the circular cross-sectional area of second body section 40 gradually increases from second body section first end 42 to second body section second end 44. Also in this embodiment, the diameter of second body section 40 adjacent second body section first end 42 is larger than the diameter of first body section 20 at first body section second end 24. Thus, in this embodiment, second body section first end 42 also defines a second body shoulder 43 which extends from and attaches second body section 40 to first body section 20 at first body section second end 24. In this embodiment, second body shoulder 43 is substantially perpendicular to first body section outer surface 28 but not to second body section inner surface 46. Preferably, second body shoulder 43 is sized and constructed so that second body section 40 is co-axially aligned with first body section 20.

Figure 3:
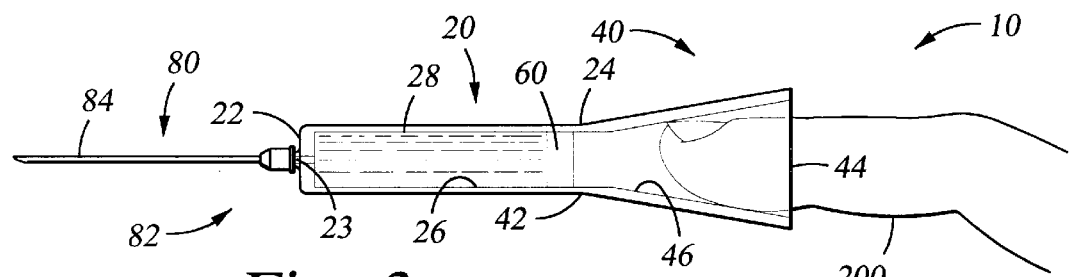
FIG. 3 is an elevational view of the syringe with a third embodiment of second body section.

In another preferred embodiment as shown in FIG. 3, second body section 40 is also frustoconical in shape and has a circular cross-sectional area In this embodiment, the circular cross-sectional area of second body section 40 gradually increases from second body section first end 42 to second body section second end 44. In this embodiment however, second body section first end 42 is completely open and its cross-sectional diameter is substantially equal to the diameter of first body section 20. Thus, in this embodiment, second body section first end 42 does not define a second body shoulder 43 as in the embodiments disclosed in FIGS. 1 and 2. Preferably, second body section 40 is sized and constructed and is attached to first body section 20 so that second body section 40 is co-axially aligned with first body section 20.

Figure 4:
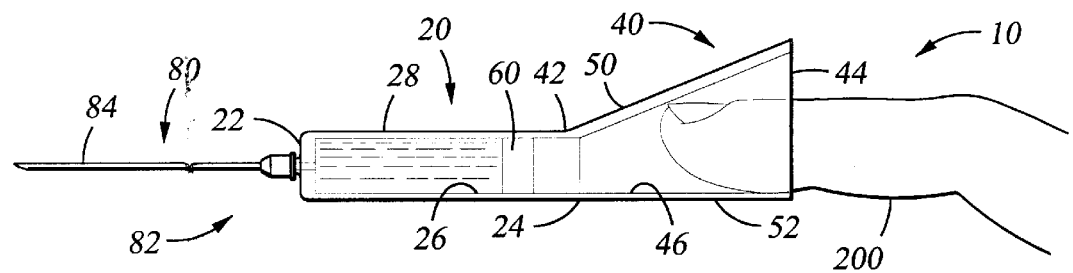
FIG. 4 is an elevational view of the syringe with a fourth embodiment of second body section.
Figure 5:
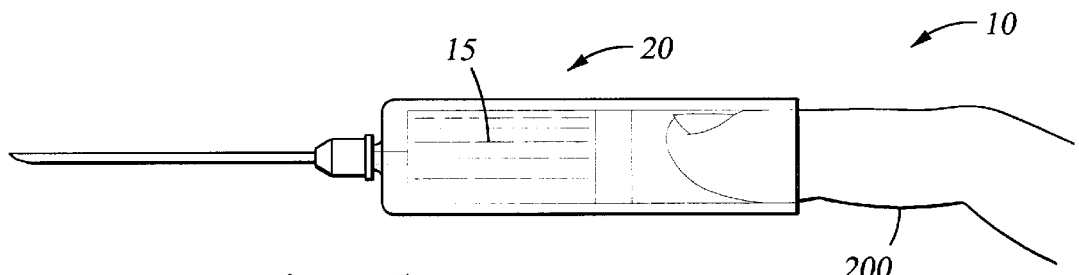
FIG. 5 is an elevational view of another embodiment of the syringe which does not include a second body section but with which my syringe application method may be utilized.

In another preferred embodiment as shown in FIG. 4, the shape of second body section 40 is frustoconical on a first side 50 and continues the line of first body section 20 on the second side 52. In this embodiment, the cross-sectional area of second body section 40 at second body section first end 42 is circular in shape. After second body section first end 42 and until second body section second end 44, the cross-sectional area of second body section 40 can be generally elliptical or circular in shape, depending on the embodiment. In addition, the cross-sectional area of second body section 40 gradually increases from second body section first end 42 to second body section second end 44. In this embodiment however, second body section first end 42 is completely open and its cross-sectional diameter is substantially equal to the diameter of first body section 20. Thus, in this embodiment, second body section first end 42 does not define a second body shoulder 43 as in the embodiments disclosed in FIGS. 1 and 2.

In another preferred embodiment as shown in FIG. 9, second body section 40 is tubular in shape and has a circular cross-sectional area In this embodiment, the circular cross-sectional area of second body section 40 is uniform from second body section first end 42 to second body section second end 44. Also in this embodiment, the diameter of second body section 40 is smaller than the diameter of first body section 20. First body section second end 24 thus defines a first body shoulder 25 which extends from and attaches second body section 40 to first body section 20 at first body section second end 24. In this embodiment, first body shoulder 25 is substantially perpendicular to both first body section outer surface 28 and second body section inner surface 46. Preferably, first body shoulder 25 is sized and constructed so that second body section 40 is co-axially aligned with first body section 20.

Seal 60 is slidingly disposed within first body section 20. Seal 60 provides a seal against first body section inner surface 26 thereby prohibiting fluid flow within first body section 20 across seal 60. A person with ordinary skill in the art will recognize that seal 60 corresponds to the sliding plunger seal 13 of prior art syringes without the attached plunger rod 12 (as shown in FIG. 8).

Fluid transmission means 80 provides fluid communication between the interior of first body section 20 and the exterior of syringe 10. Generally, when used directly on patients, fluid transmission means 80 comprises needle attachment means 82 and needle 84. Needle attachment means 82 and needle 84 are well-known in the art. In general, needle attachment means 82 is attached at one end to first end opening 23 of first body section 20 and at its other end to needle 84. Needle attachment means 82 provides fluid communication between the interior of first body section 20 and needle 84. Needle 84 in turn includes a lancing means to pierce the skin of a patient and provides fluid communication between the exterior of syringe 10 and its own interior.

It is noted that this disclosure primarily exemplifies fluid transmission means 80 as being inserted or lanced into a patient or vial. It is understood that fluid transmission means 80 may, of course, also comprise a structure which allows for syringe 10 to be inserted into a saline bag port or an IV line. Such a structure (not shown in the Figures), widely known in the art, is also expressly included within fluid transmission means 80. Thus, it is understood that fluid transmission means 80 does not necessarily require a needle 84 to enable the function of syringe 10. Indeed, syringes are widely used without needles 84 simply to transfer liquid from one location to another, to suction liquid out of one location, or to inject liquid into a location that does not require a puncture (i.e., a medical instrument port). The only critical function of fluid transmission means 80 is to provide fluid communication between the interior and exterior of syringe 10.

In the preferred embodiment of my invention, second body section 40 is selectively removably attached to first body section 20 by way of body attachment means 100. Body attachment means 100 allows the disposal of used first body sections 20.

In one embodiment as shown in FIG. 6, body attachment means 100 comprises first body section threading 102 and matching second body section threading 104. First body section threading 102 is preferably located on first body section outer surface 28 adjacent first body section second end 24. Second body section threading 104 is located on second body section first end 42. More specifically, in those embodiments including second body shoulder 43, second body threading 104 is located on second body shoulder 43. First body section threading 102 cooperatively engages second body section threading 104 to provide a secure but removable attachment between first body section 20 and second body section 40.

In another embodiment as shown in FIG. 7, body attachment means 100 comprises a second body slip ring 110. Second body slip ring 110 is fixedly attached to second body section 40 at second body section first end 42. More specifically, in those embodiments including second body shoulder 43, second body slip ring 110 is located on second body shoulder 43. Second body slip ring 110 extends from second body section first end 42 (or second body shoulder 43 in the relevant embodiments) in a direction normal to second body section first end 42 (or second body shoulder 43 in the relevant embodiments) away from second body second end 44.

In this embodiment, second body slip ring 110 includes an outer surface 112 and a circular cross-sectional area. The cross-sectional diameter of second body slip ring outer surface 112 is substantially equal to the cross-sectional diameter of first body section inner surface 26. Thus, second body slip ring 110 is insertable within first body section 20 at first body section second end 24 so that second body slip ring outer surface 112 tightly abuts and is held within first body section inner surface 26. The tight abutment between second body slip ring outer surface 112 and first body section inner surface 26 provides a secure but removable attachment between first body section 20 and second body section 40.

It is noted that FIGS. 6 and 7 illustrate the selectively removable attachment of first body section 20 to second body section 40 so that second body section first end 42 mates with first body section second end 24 and so that second body section second end 44 is distal to first body section 20. It is understood that, with simple changes to the structure of the invention, such as by changing the direction of first body section threading 102 and matching second body section threading 104 or by including another second body slip ring extending in the direction of second body second end 44, first body section 20 can selectively removably attach to second body section 40 so that second body section first end 42 mates with first body section second end 24 and so that second body section second end 44 is proximate first body section first end 22. In addition, the attachment means of first body section 20 may be included adjacent first body section first end 22 so that first body section first end 22 mates with second body section first end 42 and so that first body section second end 24 is proximate second body section second end 44. It is understood that body attachment means 100 anticipates each of these directions and methods of attachment.

It is also noted that, when syringe 10 is not in use and when second body section 40 is attached to first body section 20, a user may wish to store cotton balls or bandages inside of second body section 40 (through open second body section second end 44). Thus, immediately prior to use of syringe 10 on a patient, a user may remove the cotton balls and bandages and subsequently use such items to treat the patient's skin prior to injection and the patient's puncture caused by fluid transmission means 80 after injection.

IN OPERATION

In operation, syringe 10 may either inject medical solution located within first body section 20 into a location exterior of syringe 10 or syringe 10 may suction fluids from a location exterior of syringe 10 into first body section 20.

In the injection procedure, medical solution 15 is disposed within first body section 20 intermediate seal 60 and first body section first end 22. As in normal injection procedures, a medical provider first inserts the fluid transmission means 80 of syringe 10 into the appropriate location.

Once the fluid transmission means 80 is properly inserted in the appropriate location, the medical provider then holds syringe 10 with one hand and next inserts one finger 200 of the other hand into second body section 40 through second body section second end 44. The medical provider must ensure that finger 200 substantially covers second body section second end 44 thereby effectively providing a seal between the exterior and interior of second body section 40. Next, the medical provider must gradually, repeatedly, and preferably slowly rub second body section inner surface 46 with finger 200 in the direction of seal 60. Preferably, each rubbing motion of finger 200 continues in the direction of seal 60 as far as possible in such direction. The gradual and repeated rubbing motion of finger 200 causes the air sealed between seal 60 and finger 200 (the seal being provided by finger 200 substantially covering second body section second end 44) to be forced against seal 60 thereby increasing the pressure against seal 60 in the direction of fluid transmission means 80. Eventually, the force and pressure exerted on seal 60 by the rubbing motion of finger 200 causes seal 60 to slide and move within first body section 20 in the direction of first body section first end 22. The movement of seal 60 in the direction of first body section first end 22 in turn causes medical solution 15 to flow out of first body section 20, through first body section first end opening 23 and fluid transmission means 80, and into the selected location.

In the suction procedure, the medical provider should first ensure that seal 60 is proximate first body section first end 22. If not, the medical provider may simply move seal 60 towards first section first end 20 by use of the rubbing motion detailed herein in the injection procedure or by directly pushing seal 60 with finger 200. The medical provider then inserts fluid transmission means 80 into the appropriate location. Once the fluid transmission means 80 is properly inserted in the appropriate location, the medical provider next inserts one finger 200 into second body section 40 through second body section second end 44. Preferably, finger 200 is inserted into second body section 40 as far as possible towards seal 60. The medical provider must ensure that finger 200 substantially covers second body section second end 44 thereby effectively providing a seal between the exterior and interior of second body section 40. Next, the medical provider must gradually, repeatedly, and slowly rub second body section inner surface 46 with finger 200 in the direction away from seal 60. The gradual and repeated rubbing motion of finger 200 and the effective seal provided by finger 200 (as it substantially covers second body section second end 44) causes a suction or negative pressure at seal 60 in the direction of second body section second end 44. Eventually, the suction pressure exerted on seal 60 by the rubbing motion of finger 200 causes seal 60 to slide and move within first body section 20 in the direction of second body section second end 44. The movement of seal 60 in the direction of second body section second end 44 in turn causes a suction pressure to be created within first body section 20 and fluid transmission means 80. The suction pressure within first body section 20 and fluid transmission means 80 causes the desired fluid to be suctioned out of the selected location, through fluid transmission means 80 and first body section first end opening 23, and into first body section 20.

It is understood that, in most cases, finger 200 does not and cannot come into contact with seal 60 in either the injection procedure or the suction procedure. In fact, as previously disclosed herein, the cross-sectional diameter of one embodiment of first body section 20 is such that finger 200 would not fit within first body section 20. However, in those syringes 10 in which the cross-sectional diameter of first body section 20 is such that finger 200 could fit within first body section 20, it is understood that, in the injection procedure and/or in preparing for the suction procedure, a user may push seal 60 with finger 200 until recourse to the rubbing motion procedure is necessary. Such recourse will, of course, be necessary when finger 200 can no longer reach seal 60.

In the embodiment including body attachment means 100, second body section 40 may be selectively removed from first body section 20. Body attachment means 100 allows for first body section 20, including fluid transmission means 80, to be disposed after use. Such disposal is prudent under widely-accepted safety guidelines. It is understood that second body section 40 does not contact either the solution 15 or the patient and is thus not contaminated during the injection or the suction procedures. Undisposed second body section 40 may then be attached to and used with a new first body section 20 thereby enabling repeated cost-effective use of second body section 40.

As will be obvious from FIG. 5, the method of use for syringe 10 does not require the inclusion of second body section 40 so long as the cross-sectional diameter of first body section 20 is large enough to allow the insertion of finger 200. In this embodiment, finger 200 rubs against first body section inner surface 26. Once again, it is understood that, in most cases, finger 200 does not and cannot come into contact with seal 60. However, in those syringes 10 in which the cross-sectional diameter of first body section 20 is such that finger 200 could fit within first body section 20, it is understood that, in the injection procedure and/or in preparing for the suction procedure, a user may push seal 60 with finger 200 until recourse to the rubbing motion procedure is necessary. Such recourse will, of course, be necessary when finger 200 can no longer reach seal 60. In fact, the length of a substantial number of syringes 10 which are currently used in the medical profession is such that finger 200 would not be long enough to contact seal 60 when seal 60 is closer to first body section first end 22.

As a final note, the method of use for syringe 10 disclosed herein will function for different volumetric capacities of syringe 10. For the injection procedure, the Applicant has learned through experimentation that syringes 10 with a volumetric capacity of up to 10 mL function best (i.e., 1, 2, 5, and 10 mL syringes). For the suction procedure, the Applicant has learned through experimentation that syringes 10 with a volumetric capacity of up to 20 mL function well. The difference in volumetric capacity between the injection and the suction procedures is due to the fact that, in the suction procedure, there is more room within syringe 10 to insert finger 200 and, in the suction procedure, finger 200 follows a more natural motion.

The foregoing disclosure and description of the invention is illustrative and explanatory thereof. Various changes in the details of the illustrated construction may be made within the scope of the appended claims without departing from the spirit of the invention. The present invention should only be limited by the following claims and their legal equivalents.

I claim:

1. A syringe, comprising:
    a tubular first body section having a first body section first end and a first body section second end;
    a seal slidingly disposed within said first body section between said first body section first end and said first body section second end;
    said seal prohibiting fluid flow therethrough within said first body section;
    a fluid transmission means in fluid communication with said first body section first end and in fluid communication with the exterior of said syringe;
    a second body section having a second body section first end and a second body section second end, each of which is open;
    said second body section first end attached to said first body section second end thereby providing fluid communication between said first body section and said second body section;
    said second body section having a length and cross-sectional area sized and shaped to allow the insertion of a person's finger therein so that said finger substantially covers the opening of said second body section second end when said finger is inserted within said second body section thereby creating an effective seal on said second body section;
    said first body section having a circular cross-sectional area;
    said first body section cross-sectional area being uniform from said first body section first end to said first body section second end;
    said second body section is frustoconical in shape having a circular cross-sectional area;
    said second body section cross-sectional area gradually increasing from said second body section first end to said second body section second end;
    said second body section cross-sectional area at said second body section first end being larger than said first body section cross-sectional area;
    said second body section first end defining a second body shoulder; and
    said second body shoulder extending from and attaching said first body section second end to said second body section.

2. A syringe as in claim 1, wherein:
    said first body section including a first body section outer surface; and
    said second body shoulder being substantially perpendicular to said first body section outer surface.

3. A syringe as in claim 2, wherein said second body shoulder is sized and constructed so that said second body section is co-axial with said first body section.

4. A method of transmitting a fluid from a syringe, said syringe including an open end having a cross-sectional area sized and constructed to allow the insertion of a person's finger therein, a seal slidingly disposed within the body of said syringe, and a fluid transmission means with said fluid disposed intermediate said seal and said fluid transmission means, comprising:
    inserting a finger within said syringe through said syringe open end;
    substantially covering said syringe open end with said finger thereby creating an effective seal on said syringe open end with said finger;
    rubbing the inner surface of said syringe with said finger in the direction of said seal;
    ensuring the continuous presence of said effective seal created by said finger during said rubbing step;
    whereby said rubbing step causes the air sealed between said seal and said finger to be forced against said seal thereby causing said seal to slide towards said fluid transmission means; and
    whereby said seal movement forces and transmits said fluid out of said syringe through said fluid transmission means.

5. A method as in claim 1, wherein said rubbing step comprises gradually, repeatedly, and slowly rubbing said syringe inner surface.

6. A method of suctioning fluid into a syringe, said syringe including an open end having a cross-sectional area sized and constructed to allow the insertion of a person's finger therein, a seal slidingly disposed within the body of said syringe, and a fluid transmission means, comprising:
    positioning said fluid transmission means in the source of said fluid;
    inserting a finger within said syringe through said syringe open end;
    substantially covering said syringe open end with said finger thereby creating an effective seal on said syringe open end with said finger;
    rubbing the inner surface of said syringe with said finger in the direction away from said seal;
    ensuring the continuous presence of said effective seal created by said finger during said rubbing step;
    whereby said rubbing step causes a suction or negative pressure to be created at said seal in the direction of said finger thereby causing said seal to slide towards said finger;
    whereby a suction or negative pressure is created at said fluid transmission means in the direction of said seal thereby causing said fluid to flow into said syringe through said fluid transmission means.

7. A method as in claim 6, wherein said rubbing step comprises gradually, repeatedly, and slowly rubbing said syringe inner surface.

* * * * *